United States Patent [19]

Lawrence et al.

[11] Patent Number: 4,701,306
[45] Date of Patent: Oct. 20, 1987

[54] CONCENTRATOR FOR DETECTION OF AMINE VAPORS

[75] Inventors: André H. Lawrence, Ottawa; Lorne Elias, Nepean, both of Canada

[73] Assignee: Canadian Patents & Development Ltd., Ottawa, Canada

[21] Appl. No.: 617,575

[22] Filed: Jun. 5, 1984

[51] Int. Cl.[4] .......................... G01N 1/00; G01N 1/22
[52] U.S. Cl. ..................... 422/101; 422/60; 422/88; 436/111; 436/178
[58] Field of Search ............ 422/56, 60, 85, 88, 422/61, 169, 171, 122, 83, 101; 436/178, 111, 112, 113, 114, 115; 55/74; 423/245

[56] References Cited

U.S. PATENT DOCUMENTS

| | | | |
|---|---|---|---|
| 1,441,696 | 1/1923 | McNeil et al. | 423/245 |
| 3,168,378 | 2/1965 | Maresh et al. | 436/115 |
| 4,003,257 | 1/1977 | Fletcher et al. | 436/178 |
| 4,249,904 | 2/1981 | Rounbehler et al. | 437/107 |
| 4,332,591 | 6/1982 | Oi et al. | 436/114 |
| 4,381,408 | 4/1983 | Rounbehler et al. | 436/111 |

FOREIGN PATENT DOCUMENTS 2610963  9/1977  Fed. Rep. of Germany .......... 55/74

OTHER PUBLICATIONS

Pellizzari et al., *Anal. Chem.* 1984, vol. 56, pp. 793-798.
Hawley, ed.; *The Condensed Chemical Dictionary*, 10th ed., 1981, pp. 930-931.

Primary Examiner—Barry S. Richman
Assistant Examiner—C. M. Delahunty
Attorney, Agent, or Firm—Alan A. Thomson

[57] ABSTRACT

A method, and air sampler concentrator, for sampling and detecting trace quantities of amine vapors in ambient atmospheres, are described. Atmospheres containing vapors of amines, particularly aralkyl amines such as amphetamines, are sampled and vapors collected in a concentrator having two adsorber components, one a polymeric adsorbent for amines and the other a selected alkaline adsorbent. Collected vapors are thermally desorbed in stages and the amine vapors analyzed by gas chromatography. The concentrator and method are very suitable for detecting trace amount of amine drugs and alkyl or arylalkyl amine vapors found in some industrial work environments.

9 Claims, 2 Drawing Figures

Sample Transfer or Septum Injection

Sample Analysis or Standby Mode

Sample Transfer or Septum Injection

CONCENTRATOR FOR DETECTION OF AMINE VAPORS

This invention is concerned with the sampling and detection of trace amounts of amine vapors present in ambient atmospheres. Of particular concern is the sampling and detection of trace amounts of amine drugs such as amphetamines and alkyl or arylalkyl amine vapors found in some work environments.

BACKGROUND AND PRIOR ART

There are many situations where it is useful to be able to detect trace amounts of amine vapors in ambient atmospheres, important ones being the hidden transport of drugs for illicit purposes, and amine air pollutants to which some workers are exposed.

Amphetamine or 2-amino-1-phenylpropane is an important drug with different pharmacological effects, including analeptic effects and is employed clinically in many areas. Unfortunately, amphetamine and its N-methyl homolog, methamphetamine, are also chemically synthesized in clandestine or illegal laboratories with the goal of supplying drugs of abuse to the illicit market.

A number of analytical methods are available for the identification and determination of amphetamine in various matrices. Recently, A. H. Lawrence and J. D. MacNeil (Anal. Chem., 54, 2385-2387, 1982) reported a method for the identification of amphetamine in street drug preparations by second derivative ultraviolet spectrometry. Numerous papers have been published describing gas chromatographic methods for the determination of amphetamine and other phenyl-alkylamine derivatives in blood, urine and other liquid biological extracts (Chromatography of Environmental Hazards, Vol. IV, L. Fishbein, Elsevier Scientific Publishing Co., N.Y. 1982, p. 311). J. K. Baker (Anal. Chem, 49, 906-908, 1977) reported the use of a gas chromatographic system equipped with dual flame ionization and nitgrogen-selective rubidium bead detectors for the identification of amphetamine, methamphetamine and other illicit drugs.

The detection of some aliphatic amines in air by adsorption onto silica gel followed by acid liquid extraction, making the extract alkaline and analyzing an aliquot of the alkaline solution by GC has been reported [National Institute for Occupational Safety and Health, Manual of Analytical Methods (Second Section) Part I, U.S. Department of Health, Education and Welfare, (NIOSH), Publ. 274-845, Cincinnati, 1977]. This latter method has a detection limit of 0.01 mg. R. H. Brown and C. J. Purnell (J. Chromatogr., 178, 79-90, 1979) investigated the capacity of a Tenax-GC [trademark] adsorber to collect vapors of a variety of organic compounds including methylamine, ethylamine, propylamine, pyridine and aniline.

In the patent literature, U.S. Pat. No. 3,711,251, L. H. Goodson et al describes, in the context of detecting alcohol or aldehyde vapors in air, an absorber-reactor containing soda lime to remove electrovalent halogen compounds downstream of a converter. U.S. Pat. No. 4,003,257, J. C. Fletcher for A. Zlatkis, describes analysis in a gas chromatographic system for trace amounts of organic volatiles in which the volatiles are trapped on a porous polymer (Tenax-GC) and, in some cases, a water condensor may be used upstream of the porous polymer. U.S. Pat. No. 4,194,884, Rounbehler et al, uses Mg or Ca silicate adsorbents for air sampling then flushes the adsorbent with solvent. U.S. Pat. No. 3,327,575, Locker, uses a magnesium salt or activated alumina to adsorb interfering materials in advance of the primary adsorber.

C. E. Andre and A. R. Mosier (Anal. Chem. 45, p. 1971-1973, 1973) reported a gas chromatographic system capable of analyzing aqueous solutions of salt of short-chain aliphatic amines. The GC inlet was modified with a short Ascarite [trademark for asbestos coated with NaOH] precolumn for releasing the free amines from their salts.

The prior art evidently has not provided a simple method of detecting trace amounts of amines, such as amphetamines, in ambient atmospheres. Using techniques similar to those in U.S. Pat. No. 4,003,257, we have tried to detect traces of amphetamines in air and were unsuccessful. The adsorbed amine was being altered in some manner.

SUMMARY OF THE INVENTION

We have found that using a novel two-component sampler-concentrator and desorbing in two stages with venting enabled good results to be achieved.

The invention includes an air sampler concentrator comprising:

(a) a polymeric adsorbent which adsorbs and preferentially retains amines on heating to temperatures sufficient to desorb moisture, and (b) a selected alkaline adsorbent material which neutralizes acids and readily releases amines and moisture on heating, (b) being positioned so as to minimize access of moisture and acids to (a).

The invention further includes a method of detecting trace amounts of amine vapors in ambient atmospheres including moisture and acidic gases comprising:

(i) circulating the atmosphere through a sampler concentrator comprising (a) a polymeric adsorbent which adsorbs and preferentially retains amines on heating to temperatures sufficient to desorb moisture, and (b) a selected alkaline adsorbent material which neutralizes acids and readily releases amines and moisture on heating, (b) being positioned so as to minimize access of moisture and acids to (a), until significant amounts of any amine vapors present have been adsorbed, (ii) heating the concentrator to a temperature and for a time sufficient to desorb moisture and amine but not acids from (b) and moisture but not amine from (a) and venting the desorbed moisture vapors, and (iii) further heating the concentrator to a temperature and for a time sufficient to desorb amine from (a) and conducting the desorbed amine vapors to detecting means.

For best results, the selected alkaline adsorbent should contact the incoming atmosphere before it reaches the polymeric adsorbent so as to minimize access of moisture and especially acids to the polymeric adsorbent.

DETAILED DESCRIPTION AND PREFERRED EMBODIMENTS

Figure 2:
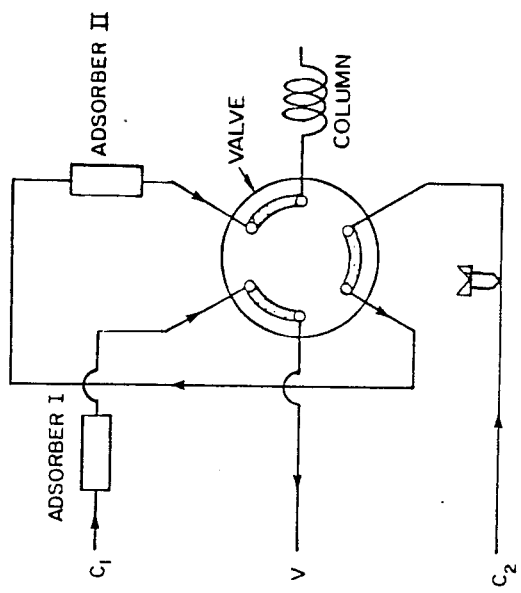
FIG. 2 is a similar schematic of the flow paths for sample transfer to the column from Adsorber II, and for venting Adsorber I.

In the sampler concentrator, adsorbent (a) will normally be a non-reactive organic polymer having an affinity for amines and stable at the amine desorption temperatures, usually a porous, highly aromatic, organic polymer stable to relatively high temperatures, e.g. 300° C. Preferably, the polymer is one based on the monomer 2,6-diphenyl-p-phenylene oxide. Particularly preferred is the polymer known as Tenax-GC [trademark of Akzo Res. & Eng. N.V., Arnhem, Netherlands]. The particle size is suitably about 35-60 mesh (U.S. Sieve) but this is not critical.

Adsorbent (b) will normally be an inorganic porous material of alkaline nature particularly one which retains its porosity on exposure to moisture. This adsorbent should also retain and neutralize acidic material. Various alkaline siliceous adsorbents have been tried but they lost porosity after one cycle, i.e. they would only be useful on a "one shot" basis. It was found that soda lime fulfilled all of the criteria and was suitable for repeated sampling and desorption without loss of porosity. Preferably, the soda lime (calcium oxide with about 5-20% sodium hydroxide) has a particle size within the range of about 10-20 mesh (U.S. Sieve).

In the sampler concentrator, one way of positioning the adsorbents is to have a constriction or support downstream which retains an inert porous first plug of fine porosity able to retain the polymeric adsorbent. The polymeric adsorbent upstream may be positioned between two such plugs with the alkaline adsorbent upstream of and retained against the second plug, e.g. by a third such plug. The plugs may be of a glass wool, the surface of which has been silanized to render it inert, or other inert porous materials, such as polytetrafluoroethylene and platinum or nickel screens may be used.

The proportion of polymeric adsorbent (a) normally is from about 100 to about 200% by wt. of alkaline adsorbent (b): in some cases, other proportions may be found suitable. An exess of adsorption and neutralization capacity should usually be present.

In method step (ii), the sample concentrator is heated to, e.g. within about 50°-250° C. to desorb moisture yet retain the amine on the polymeric adsorbent. The desorbed moisture is vented without allowing it to proceed to the detecting means. In step (iii) the concentrator is heated above 70° C. usually to within about 150°-300° C. to desorb amine which is conducted to detecting means. It has been found preferable to conduct the desorbed amine to a second adsorber where it can be concentrated and released all together, thus giving greater sensitivity. Adsorbents in the second adsorber are of the type which has high affinity for amines but quickly releases them at lower temperatures, e.g. of about 70° to 250° C. Suitable adsorbents for Adsorber II include solid organopolysiloxanes, polyethyleneglycol succinate, etc., which are known to the art.

The detecting means suitably comprises a gas chromatograph column with a packing of the organopolysiloxane type, or capillary columns with a suitable coating, and detecting means selective for nitrogen. Suitable detecting means include any nitrogen selective detectors known for this purpose.

Various amines which are unaltered by the adsorbants can be subject to sampling and detection. Alkyl amines, such as ethylamine and propylamine (alkyl group of 1-6 carbon atoms), are suitable inter alia for detection. Of particular interest are aralkyl amines, e.g. phenylalkyl amines where the alkyl group has from 1 to 6 carbon atoms. Examples include phenylethyl amine, amphetamine and methamphetamine.

The polymeric adsorbent - soda lime sampler concentrator has been found very suitable for repeated usage.

The following example is illustrative.

EXAMPLE

The sampler concentrator used in these tests was constructed of glass tubing 75 mm × 6.3 mm O.D. with a restriction in the middle and contained about 30 mg of Tenax-GC (35-60 mesh). The Tenax adsorbent was held in place with small plugs of silanized glass wool. In most tests, the alkaline adsorbent was held in place with a further plug of the treated glass wool. The tubes were conditioned overnight at 250° C. in a helium stream at a flow rate of 50 cm$^3$/min. Before use a chromatogram was recorded to check the purity of each tube. Neither peaks nor baseline drift were observed for tubes conditioned and then stored for up to 3 days. Air was drawn through the tubes by a diaphragm pump connected to a flow meter with ballast volume.

To provide a controlled vapor source, a continuous stream of lab-compressed air (purified by an oil mist microfilter followed by a bed of activated charcoal) was generated to contain a constant concentration of amphetamine vapor in a dynamic dilution system as described by M. Krzymien and L. Elias [J. Phys. (E) Sci. Instrum., 9, 584-586, 1976]. For accurate sampling, the flow rate of vapor exiting the vapor source was maintained greater than the sampling rate by a factor of two or more.

Amphetamine after desorption, was analyzed on a Varian [trademark] 1400 gas chromatograph equipped with a nitgrogen-phosphorous thermionic specific detector.

A second adsorber (Adsorber II in FIGS. 1 and 2) was inserted in the system, which contained about 30 mg of polyethylene glycol succinate [Ultrabond PEGS - trademark].

The chromatographic conditions were as follows:

Column: 2 m × 3.2 mm O.D. nickel tube packed with 100-120 mesh. 3% of methyl silicone polymer [OV-101—trademark]on a support of Chromosorb W [trademark]

Carrier gas: helium at a flow rate of 50 cm$^3$/mm.

Oven temperature: 160° C.

Adsorber I heater temperature: 250° C.

Adsorber II heater temperature: approximately 250° C.

Detector temperature: 250° C.

Detector hydrogen pressure and air flow rate were 16 PSIG and 250 cm$^3$/min, respectively.

Rubidium glass bead electrically heated at current and bias voltage settings of 7.0 and −4.0, respectively.

The signal from the detector was recorded on a strip chart reporting integrator.

After sampling, the sampler concentrator was connected to the gas chromatograph system. The adsorbed amine vapors were removed by heating (after venting moisture with helium carrier gas $C_1$ for 40 seconds at 250° C., $C_1$ to V in FIG. 2) also at 250° C., again flushing with a helium carrier stream ($C_1$ in FIG. 1) to Adsorber II. The vapors were subsequently desorbed at about 250° C. for injection into the chromatographic column. A six-port switching valve provided the various flow paths involved in the repeated analyses as in FIGS. 1 and 2. The recorded amphetamine peak area was compared with that of an amphetamine standard solution deposited directly on the Tenax adsorber and analyzed in the same manner as the air samples. The concentration of this standard solution was $6 \times 10^9$ amphetamine/microliter.

A number of materials were examined as possible adsorbents for trapping amphetamine vapors. Silica gels and activated charcoals strongly retained the amine vapors which could not be released by thermal desorption. Only polymeric adsorbents which thermally released the amine vapors proved adequate, such as Tenax-GC. Flow rates of the order of 1 L/min were easily achieved with the Tenax; no loss of amphetamine occurred through 30 mg of Tenax for 120 L of nitrogen or purified air; the mean recovery for amphetamine from Tenax over the range 20–50 ng added was greater than 90%; the desorption temperature of ca. 250° C. was low enough to prevent decomposition while providing a desorption time which was sufficiently short to allow for a 5 min. total analysis cycle.

The efficiency of the Tenax adsorber was tested by measuring the vapor concentration as a function of the sampling rate. The plot of the measured vapor concentration in the sampling port of the vapor source as a function of the sampling rate was found to be linear with a correlation coefficient of 0.996 and a precision of +4%. Each experimental point on the line was the average of at least three analyses.

It was found that no loss of amphetamine occurred through a sampler concentrator containing only 30 mg of Tenax-GC per se for 120 L of purified air or nitrogen. However, serious losses occurred when these experiments were repeated using ambient air. It was found that after purging with 6 L of ambient air, no trace of amphetamine could be detected on the chromatogram. The latter experiments were repeated using two Tenax adsorbers in series. After purging with 6 L of ambient air, the adsorbers were analyzed in the usual manner. No amphetamine peak could be observed on either chromatogram. It was therefore concluded that amphetamine vapors did not elute from the first adsorber but were probably irreversibly retained on the Tenax due to the effect of some acidic impurities present in ambient air.

The experiments were repeated using a Tenax-Ascarite two-component adsorber sampling system. 20 ng of amphetamine in n-hexane were deposited with a syringe directly on the front (upstream) section of the sampler concentrator and 6 L of ambient air were drawn through. The recovery of amphetamine from the dual adsorber after air sampling was quantitative. However, upon exposure to moisture and carbon dioxide, Ascarite lost its granular shape creating a significant flow restriction in the adsorber tubes. Ascarite-type adsorbers could be used on a once only basis.

Repeated tests showed that the preferred alkaline material (found able to fulfill all necessary functions) was sodium calcium hydrate (soda lime). The recovery of amphetamine from a dual soda lime/Tenax-GC adsorber system, after purging with 60 L of ambient air, was also quantitative and this system was used successfully in many experiments.

Some initial field tests were carried out. Although the distances from the source were small, the data from this preliminary field experiment indicated that amphetamine can be efficiently detected in ambient air using a two-component soda lime/Tenax-GC adsorber followed by gas chromatographic analysis with a nitrogen selective detector. The detection limit for amphetamine based on a signal-to-noise ratio greater than 3 was 2 ng. The actual air concentration corresponding to this limit is 5 parts per trillion or 0.03 micrograms/m$^3$.

Repetitive use of the sampling adsorbers over long periods of time revealed some problems associated with buildup of interfering background material. Replacement of the used soda lime with fresh, followed by conditioning as described above, eliminated the problem, permitting the costly Tenax-GC to be used repeatedly.

In the above Example, in the desorption and venting of moisture followed by desorption of the amine, the same temperature (250° C.) was used in the sampler concentrator. The moisture was released first and vented for an interval (40 sec) sufficient to remove substantially all moisture but found insufficient to allow desorbing the amine from the Tenax. Alternatively, the moisture could have been desorbed at a lower temperature and vented, then the temperature raised to desorb the amine. Various time of venting-temperature combinations can be used depending on the particular system and amine.

Figure 1:
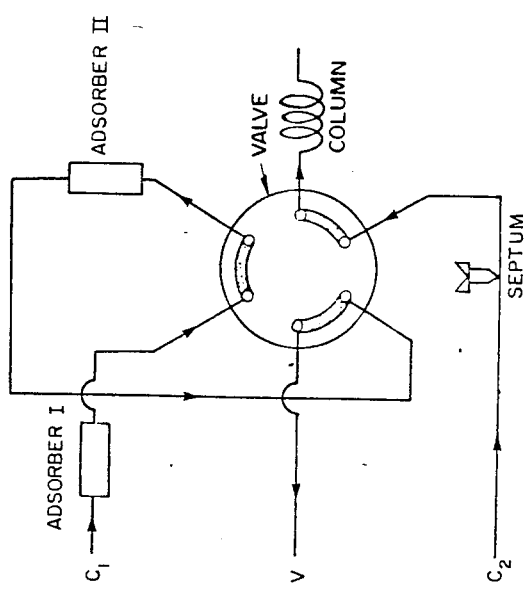
FIG. 1 is a schematic diagram of the flow paths through the Adsorbers I and II and via a six-port valve to vent, and for septum injection to the column.

Referring to the drawings, in FIG. 2, the flow path $C_1$ to V depicts the venting of desorbed moisture from Adsorber I in a carrier gas stream. In FIG. 1 the flow path $C_1$ Adsorber I to Adsorber II to vent V, depicts the transfer of adsorbed amino from Adsorber I to Adsorber II using carrier gas stream $C_1$. Subsequently in FIG. 2, a second carrier gas stream $C_2$ is used to transfer amine from Adsorber II to the chromatographic column for analysis. As indicated in FIG. 1 the carrier gas $C_2$ also can be used for injection to the chromatographic column of material introduced at the septum site.

Referring to the drawings, in FIG. 2, the flow path $C_1$ to V depicts the venting of desorbed moisture of Adsorber I in a carrier gas stream. In FIG. 1 the flow path $C_1$ to Adsorber I to Adsorber II to vent V, depicts the transfer of adsorbed amine from Adsorber I to Adsorber II using carrier gas stream $C_1$. Subsequently in FIG. 2, a second carrier gas stream $C_2$ is used to transfer amine from Adsorber II to the chromatographic column for analysis. As indicated in FIG. 1 the carrier gas $C_2$ also can be used for injection to the chromatographic column of material introduced at the septum site.

What is claimed is:

1. An air sample concentrator consisting essentially of:
   (a) a porous highly aromatic organic polymeric adsorbent which adsorbs and preferentially retains amines on heating to temperatures sufficient to desorb moisture, and releases adsorbed amines at higher temperatures, said adsorbent being stable at said higher temperatures,
   (b) a soda lime alkaline adsorbent material which neutralizes acids and readily releases amines and moisture on heating, (b) being positioned upstream of (a) and being in flow communication therewith so as to minimize access of moisture and acids in an air sample to (a),
   and (c) containing-means confining (a) and (b) in place and providing flow communication between (a) and (b), and having an air inlet adjacent adsorbent (b) and an air outlet adjacent adsorbent (a).

2. The concentrator of claim 1 in which (b) is a porous form of soda lime which retains its porosity upon exposure to moisture.

3. The concentrator of claim 1 in which (a) is a polymer based on 2,6-diphenyl-p-phenylene oxide.

4. The concentrator of claim 1 in which (a) and (b) are held in place within said containing-means by inert porous retaining means.

5. The concentrator of claim 4 in which the proportion of (a) with respect to (b) is from about 100 to about 200% by wt.

6. The concentrator of claim 1 in combination with means to flow an air sample through (a) and (b) from said air inlet to said air outlet.

7. The concentrator of claim 6 in further combination with means to controllably heat (a) and (b).

8. The concentrator of claim 7 further in combination with a valve means, said valve means being in flow communication with said air outlet of said containing means and having plural valve outlets therein to which an air sample passed from said air outlet may selectively be passed, whereby one of said valve outlets can be used to vent an air sample and another of said valve outlets can be used to pass an air sample to a dector.

9. The concentrator of claim 8 in further combination with a second stage amine adsorber constructed and arranged to selectively retain and quickly release amine vapours and located downstream of the concentrator.

* * * * *